United States Patent [19]

Rovnyak

[11] 3,979,381
[45] Sept. 7, 1976

[54] THIOPYRANO[4,3-c] PYRAZOLES

[75] Inventor: George C. Rovnyak, Hopewell, N.J.

[73] Assignee: E. R. Squibb & Sons, Inc., Princeton, N.J.

[22] Filed: Aug. 11, 1975

[21] Appl. No.: 603,580

[52] U.S. Cl. ............................ 260/240 A; 260/240 F
[51] Int. Cl.² .............. C07D 231/54; C07D 495/02
[58] Field of Search ..................... 260/240 A, 240 F

[56] References Cited
UNITED STATES PATENTS

| | | | |
|---|---|---|---|
| 3,852,279 | 12/1974 | Krapcho et al. ................. | 260/240 F |
| 3,897,420 | 7/1975 | Krapcho et al. ................. | 260/240 F |
| 3,911,129 | 10/1975 | Krapcho et al. ................. | 260/240 F |

OTHER PUBLICATIONS
Chemical Abstracts vol. 81:13351n (1974).

*Primary Examiner*—Donald B. Moyer
*Attorney, Agent, or Firm*—Lawrence S. Levinson; Merle J. Smith; Donald J. Barrack

[57] ABSTRACT

Anti-inflammatory activity is exhibited by compounds having the formula

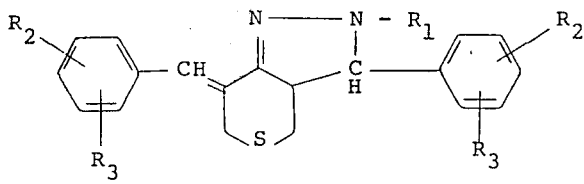

the salts thereof, and the 5-oxide and 5,5-dioxide thereof, wherein $R_1$ is hydrogen, alkyl, aryl, arylalkyl, or acyl; and $R_2$ and $R_3$ are the same or different and are hydrogen, alkyl, hydroxy, alkoxy, alkylthio, alkylsulfinyl, trifluoromethyl, halogen, acyl, cyano, nitro, or dialkylamino.

28 Claims, No Drawings

THIOPYRANO[4,3-C] PYRAZOLES

BRIEF DESCRIPTION OF THE INVENTION

Compounds having the formula

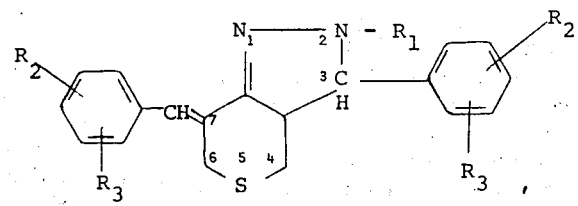

I the 5-oxide and 5,5-dioxide thereof, and the pharmaceutically acceptable acid addition salts thereof, have useful antiinflammatory activity. In formula I, and throughout the specification, the symbols are as defined below.

$R_1$ can be hydrogen, alkyl, aryl, arylalkyl, or

X—C— wherein X is alkyl or aryl; and $R_2$ and $R_3$ are the same or different and are hydrogen, alkyl, hydroxy, alkoxy, alkylthio, alkylsulfinyl, trifluoromethyl, halogen,

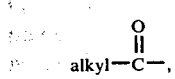
alkyl—C—, cyano, nitro, or dialkylamino.

The terms alkyl and alkoxy, as used throughout the specification (individually or as part of a larger group), refer to groups having 1 to 8 carbon atoms. Alkyl and alkoxy groups having 1 to 3 carbon atoms are preferred.

The term aryl, as used throughout the specification, refers to phenyl or phenyl monosubstituted with an alkyl, alkoxy, halogen, or trifluoromethyl group; phenyl is preferred.

The term arylalkyl, as used throughout the specification, refers to alkyl groups substituted with an aryl group. The preferred arylalkyl groups are benzyl and phenethyl.

The term halogen, as used throughout the specification, refers to fluorine, chlorine, bromine and iodine; fluorine and chlorine are preferred.

DETAILED DESCRIPTION OF THE INVENTION

The compounds of formula I (and the 5-oxides and 5,5-dioxides thereof) are prepared using as starting materials a substituted tetrahydro-4H-thiopyran-4-one having the formula

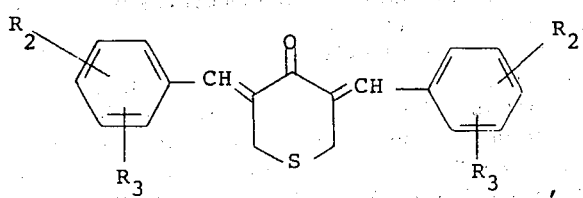

II or a 1-oxide or 1,1-dioxide thereof, and a hydrazine having the formula $H_2NNH-R_1$   III The compounds of formulas II and III are readily obtainable; see for example, Journal of the American Chemical Society, 79:156 (1957) and Journal of Medicinal Chemistry, 7:493 (1964).

A substituted tetrahydro-4-H-thiopyran-4-one of formula II can be prepared by reacting tetrahydro-4H-thiopyran-4-one with an appropriate benzaldehyde having the formula

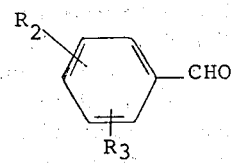   IV

The corresponding 1-oxide or 1,1-dioxide can be prepared by reacting a substituted tetrahydro-4H-thiopyran-4-one of formula II with an appropriate amount of an oxidizing agent. Treatment with meta-periodic acid in aqueous methanol at room temperature for about 12 to 48 hours gives the 1-oxide. Treatment with 30% hydrogen peroxide in acetic acid at about 100°C to 130°C for about 5 to 30 minutes gives the 1,1-dioxide.

A hydrazine of formula III can be prepared by reacting an excess of hydrazine ($H_2NNH_2$) with a compound having the formula $R_1 - Y$   V wherein Y is chlorine or bromine.

Reaction of a substituted tetrahydro-4H-thiopyran-4-one of formula II (or a 1-oxide or 1,1-dioxide thereof) with a hydrazine of formula III yields a product of formula I, or the corresponding 5-oxide or 5,5-dioxide. The reaction can be run in an organic solvent, preferably a lower alkanol such as methanol. While reaction conditions are not critical, the reaction will preferably be run at, or near, the reflux temperature of the solvent.

Alternatively, compounds of formula I wherein $R_1$ is hydrogen (and 5-oxides and 5,5-dioxides thereof) can be used as intermediates for the preparation of other compounds of formula I, by reaction with alkylating and acylating agents using procedures well known in the art.

The 5-oxide and 5,5-dioxide derivatives of a compound of formula I can, alternatively, be prepared by oxidizing the corresponding thiiopyrano[4,3-c]pyrazole of formula I. Oxidation of a compound of formula I using one equivalent of sodium periodate or hydrogen peroxide yields the corresponding sulfoxide derivative. Oxidation of a compound of formula I using potassium permanganate or excess hydrogen peroxide yields the corresponding sulfonyl derivative. Alternatively, the sulfoxide and sulfonyl derivatives can be prepared by treating compounds of formula I with m-chloroperbenzoic acid. Treating a compound of formula I, or a sulfoxide derivative of a compound of formula I, with two equivalents of m-chloroperbenzoic acid for 2 to 24 hours at room temperature (or for a shorter time with slight heating) yields the corresponding sulfonyl derivative.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

The compounds of formula I, the pharmaceutically acceptable acid addition salts thereof, and the 5-oxide and 5,5-dioxide thereof, are useful in treating inflammation in mammalian species, e.g., rats, dogs, cats, monkeys, etc. Joint tenderness and stiffness (in conditions such as rheumatoid arthritis) are relieved by the above described compounds.

The compounds of this invention can be formulated for use as anti-inflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70kg/day to 2 g/70kg/day, preferably 100 mg/70kg/day to 1 g/70kg/day.

The following examples are specific embodiments of this invention.

EXAMPLE 1

2,3,3a,4,6,7-Hexahydro-3-phenyl-7-(phenylmethylene)-2-propylthiopyrano[4,3-c]pyrazole A mixture of 5.84g of tetrahydro-3,5-bis-(phenylmethylene)-4H-thiopyran-4-one and 1.48g of n-propyl hydrazine in 100ml of methanol is heated at reflux temperature for 3 hours. Upon cooling, solids are collected and washed with methanol. Recrystallization from methanol gives 4.0g of material, melting point 111°–120°C. Two recrystallizations from acetonitrile yield 2.0g of the title compound, melting point 119.5°–122°C.

EXAMPLE 2

2,3,3a,4,6,7-Hexahydro-3-(4-methoxyphenyl)-7-[(4-methoxyphenyl)methylene]-2-propylthiopyrano[4,3-c]pyrazole A mixture of 6.0g of tetrahydro-3,5-bis-[(4-methoxyphenyl)methylene]-4H-thiopyran-4-one and 1.3g of n-propyl hydrazine in 200ml of methanol is heated at reflux temperature for 3.5 hours, and then allowed to cool to room temperature. The resultant crystals are collected by filtration and chromatographed on a dry packed neutral alumina column (Activity I). The fractions eluted with 10–20% ethyl acetate/hexane are combined and recrystallized from acetone/hexane to give 2.4g of the title compound, melting point 149.5°–151.5°C.

EXAMPLE 3

3-(4-Chlorophenyl)-7-[(4-chlorophenyl)methylene]-2,3,3a,4,6,7-hexahydro-2-propylthiopyrano[4,3-c]pyrazole A mixture of 6.0g of tetrahydro-3,5-bis-[(4-chlorophenyl)methylene]-4H-thiopyran-4-one, 1.3g of n-propyl hydrazine, and 100mg of hydroquinone in 100ml of dichloroethane is heated at reflux temperature for 2.5 hours and allowed to cool to room temperature. The reaction mixture is washed with dilute hydrochloric acid and water, and then dried over calcium chloride. After the solvent is removed in vacuo, the residue is chromatographed on a dry packed neutral alumina column (Activity I). The fractions eluted with 0-5% ethyl acetate/hexane are combined and crystallized from acetone/acetonitrile to give 2.8g of the title compound, melting point 118°–122°C.

EXAMPLE 4

2,3,3a,4,6,7-Hexahydro-3-phenyl-7-(phenylmethylene)-2-propylthiopyrano[4,3-c]pyrazole-5,5-dioxide A. Tetrahydro-3,5-bis-(phenylmethylene)-4H-thiopyran-4-one-1,1-dioxide To a slurry of tetrahydro-3,5-bis-(phenylmethylene)-4H-thiopyran-4-one in 70ml of acetic acid is added 7ml of 30% hydrogen peroxide. The mixture is stirred, heated at 130°C in an oil bath for 15 minutes, and cooled to room temperature. The product is collected by filtration, washed with acetic acid and dried in vacuo at 50°C to give 4.6g of the title compound, melting point 201°–203°C.

B. 2,3,3a,4,6,7-Hexahydro-3-phenyl-7-(phenylmethylene)-2-propylthiopyrano[4,3-c]pyrazole-5,5-dioxide A mixture of 3.24g of tetrahydro-3,5-bis-(phenylmethylene)-4H-thiopyran-4-one-1,1-dioxide and 0.6g of n-propyl hydrazine in 100ml of absolute methanol is heated at reflux temperature for 2 hours. The mixture is allowed to cool, and is then filtered to give 2.8g of crude product. The crude material is stirred for about 16 hours in 200ml of carbon tetrachloride and filtered. The mother liquor is concentrated in vacuo and the residue is crystallized from methanol to give 1.5g of the title compound, melting point 197°–199°C.

EXAMPLE 5

2,3,3a,4,6,7-Hexahydro-3-phenyl-7-(phenylmethylene)-2-propylthiopyrano[4,3-c]pyrazole-5-oxide A. Tetrahydro-3,5-bis(phenylmethylene)-4H-thiopyran-4-one-1-oxide A solution of 10.4g of sodium periodate in 50ml of water is added to a suspension of 7.0g of tetrahydro-3,5-bis-(phenylmethylene)-4H-thiopyran-4-one in 300ml of methanol. The mixture is stirred at room temperature for 3 days (a water bath is used for the first hour to moderate a slightly exothermic reaction). Solvent is removed in vacuo and the residue is stirred with chloroform and filtered. The filtrate is concentrated in vacuo and the residue is crystallized from 150ml of methanol, giving 6.4g of the title compound, melting point 155°–160°C. A second crop of 0.5g of the title compound, melting point 154°–157°C is also obtained.

B. 2,3,3a,4,6,7-Hexahydro-3-phenyl-7-(phenylmethylene)-2-propylthiopyrano[4,3-c]pyrazole-5-oxide (two isomers)

n-Propyl hydrazine (1.14g) is added to a suspension of 3.8g of tetrahydro-3,5-bis-(phenylmethylene)-4H-thiopyran-4-one-1-oxide in 75ml of methanol and the mixture is heated at reflux temperature for 2 hours. The crystals which form on cooling are collected to give 1.0g of the title compound, melting point 176°–177.5°C. The mother liquor is concentrated in vacuo and the residue is crystallized from acetonitrile/water (2:1) to yield an additional 0.6g of the title compound, melting point 176.5°–178°C. (isomer A)

The mother liquors from the major product (isomer A) are combined and recrystallized several times from acetonitrile to give 400mg of the title compound, melting point 164°–166°C (isomer B)

EXAMPLE 6

2,3,3a,4,6,7-Hexahydro-3-(4-methoxyphenyl)-7-[(4-methoxyphenyl)methylene]-2-propylthiopyran[4,3-c]pyrazole-5-oxide A solution of 4.3g of tetrahydro-3,5-bis-[(4-methoxyphenyl)methylene]-4-H-thiopyran-4-one-5-oxide and 0.9g of n-propyl hydrazine in 250ml of methanol is heated at reflux temperature for 4 hours. When the reaction mixture is cooled, unreacted starting material precipitates out and is removed by filtration. Concentration of the filtrate precipitates out 2.6g of crude product, which is collected by filtration and recrystallized from acetonitrile 4 times to yield 0.7g of the title compound, melting point 196°–198°C.

An additional 0.4g of the title compound is obtained by column chromatography of the original filtrate. A column of neutral alumina (Activity I) is used and chloroform/hexane is used as the eluant.

EXAMPLE 7

3-(4-Chlorophenyl)-7-[(4-chlorophenyl)methylene]-2,3,3a,4,6,7-hexahydro-2-propylthiopyrano[4,3-c]pyrazole-5,5-dioxide A mixture of 5.1g of tetrahydro-3,5-bis[(4-chlorophenyl)methylene]-4H-thiopyran-4-one-1,1-dioxide and 0.96g of n-propyl hydrazine in 250ml of methanol is heated at reflux temperature for 45 minutes. The solids which precipitate out are collected by filtration. The crude product is recrystallized twice from acetone/hexane to give 2.5g of the title compound, melting point 208°–210°C.

EXAMPLE 8

2,3,3a,4,6,7-Hexahydro-3-(4-methoxyphenyl)-7-[(4-methoxyphenyl)methylene]-2-propylthiopyrano[4,3-c]-pyrazole-5,5-dioxide A mixture of 4.5g of tetrahydro-3,5-bis-[(4-methoxyphenyl)methylene-4H-thiopyran-4-one-1,1-dioxide and 1.04g of n-propyl hydrazine in 250ml of methanol is heated at reflux temperature for 30 minutes and then cooled. The precipitate that forms is collected by filtration and recrystallized twice from acetone/hexane to yield 2.2g of the title compound, melting point 195°–198°C.

EXAMPLE 9

3-(3,4-Dichlorophenyl)-7-[(3,4-dichlorophenyl)methylene]-2,3,3a,4,6,7-hexahydro-2-propylthiopyrano[4,3-c]pyrazole A suspension of 6.5g of tetrahydro-3,5-bis-[(3,4-dichlorophenyl)methylene]-4H-thiopyran-4-one and 1.1g of n-propyl hydrazine in 250ml of methanol/chloroform (1:1) is heated at reflux temperature for about 16 hours. The reaction mixture is allowed to cool slightly. Unreacted starting material precipitates out and is removed by filtration. The filtrate is concentrated in vacuo, added to chloroform and washed with dilute hydrochloric acid and water. The organic layer is dried with magnesium sulfate and concentrated in vacuo to 5g of a semi-solid material. This is applied to a wet-packed (hexane) neutral alumina column (Activity I) and eluted with 0–100% ether/hexane. Elution with 10–40% ether/hexane yields the product as an oil.

EXAMPLE 10

2,3,3a,4,6,7-Hexahydro-2-propyl-3-[3-(trifluoromethyl)phenyl]-7-[[3-(trifluoromethyl)phenyl]methylene]thiopyrano[4,3-c]pyrazole-5,5-dioxide A mixture of 2.5g of tetrahydro-3,5-bis[[3-(trifluoromethyl)phenyl]methylene]-4H-thiopyran-4-one-1,1-dioxide and n-propyl hydrazine in 100ml of methanol is heated at reflux temperature for 1 hour. The crystals obtained on cooling to 5°–10°C are collected and dried in vacuo over phorphorus pentoxide at 50°C to yield 1.7g of the title compound, melting point 190°–191°C. The filtrate is diluted with water giving additional crude material which is recrystallized from methanol to give 400mg of the title compound, melting point 191°–193.5°C.

EXAMPLE 11

2,3,3a,4,6,7-Hexahydro-2-propyl-3-[3-(trifluoromethyl)phenyl]-7-[[3-(trifluoromethyl)phenyl]methylene]thiopyrano[4,3-c]pyrazole A mixture of 4.28g of tetrahydro-3,5-bis-[[3-(trifluoromethyl)phenyl]methylene]-4H-thiopyran-4-one and 962mg of n-propyl hydrazine in 150ml of methanol is heated at reflux temperature for 3 hours and then cooled to room temperature. Solids are collected and washed to give 1.3g of the title compound, melting point 90°–93.5°C. The combined mother liquor and washings are concentrated to 100ml and 15–20ml of water is added to the hot solution. Upon cooling, an additional 1.8g of material is collected and recrystallized from methanol/water to give 1.6g of the title compound, melting point 89°–93°C.

EXAMPLE 12

2,3,3a,4,6,7-Hexahydro-3-(2-methylphenyl)-7-[(2-methylphenyl)methylene]-2-propylthiopyrano[4,3-c]pyrazole A mixture of 6.7g of tetrahydro-3,5-bis-[(2-methylphenyl)methylene]-4H-thiopyran-4-one and 1.6g of n-propyl hydrazine in 250ml of methanol is heated at reflux temperature for 4 hours and allowed to cool to room temperature over a 16hour period. The precipitate that forms is collected by filtration and chromatographed on a neutral alumina column (Activity I). The fractions eluted with 10–20% ether/hexane are combined and recrystallized from methanol/water to give 1.6g of the title compound, melting point 110°–112.5°C.

EXAMPLE 13

2,3,3a,4,6,7-Hexahydro-3-phenyl-7-(phenylmethylene)thiopyrano[4,3-c]pyrazole-5,5dioxide A mixture of 5.0g of tetrahydro-3,5-bis-(phenylmethylene)-4H-thiopyran-4-one-1,1-dioxide and 600mg of anhydrous hydrazine in 300ml of methanol is heated at reflux temperature for 2 hours. The mixture is cooled in an ice bath, filtered, and the product is washed with fresh methanol. The filtrate and washings are concentrated to about 100ml and cooled in an ice bath, yielding an additional small amount of product. The combined yield is 4.7g of the title compound, melting point 202°–208°C, dec.

EXAMPLE 14

2-Acetyl-2,3,3a,4,6,7-hexahydro-3-phenyl-7-(phenylmethylene)thiopyrano[4,3-c]pyrazole-5,5-dioxide A suspension of 1.6g of 2,3,3a,4,6,7-hexahydro-3-phenyl-7-(phenylmethylene)thiopyrano[4,3-c]pyrazole-5,5-dioxide in 2ml of acetic anhydride and 30ml of acetic acid is heated on a steam bath for 15 minutes. Hot water (50ml) is added with stirring and the solution is allowed to cool to room temperature. The solids are collected and washed well with water and dried in vacuo over phosphorus pentoxide at 50°C to yield 1.65g of the title compound, melting point 218°–219.5°C.

EXAMPLE 15

3-(4-Chlorophenyl)-7-[(4-chlorophenyl)methylene]-2,3,3a,4,6,7-hexahydro-2-phenylthiopyrano[4,3-c]pyrazole-5,5-dioxide A mixture of 2.0g of tetrahydro-3,5-bis-[(4-chlorophenyl)methylene]-4H-thiopyran-4-one-1,1-dioxide and 0.6g of phenyl hydrazine in 100ml of methanol is heated at reflux temperature for 2 hours and then cooled. The precipitate is collected by filtration and recrystallized from acetone/hexane to give 1.6g of the title compound, melting point 246.5°–249°C.

EXAMPLE 16

2,3,3a,4,6,7-Hexahydro-3-[3-trifluoromethyl)-phenyl]-7-[[3-(trifluoromethyl)phenyl]methylene]thiopyrano[4,3-c]pyrazole-5,5-dioxide A mixture of 1.9g of tetrahydro-3,5-bis-[[3-(trifluoromethyl)phenyl]methylene]-4-H-thiopyran-4-one-1,1-dioxide and 170mg of anhydrous hydrazine in 100ml of methanol is heated at reflux temperature for 30 minutes. About 20ml of water is added to the hot solution, which is then allowed to cool to 5°–10°C. The solids are collected and dried in vacuo over phosphorus pentoxide at 50°C to give 1.6g of the title compound, melting point 183°–185°C.

EXAMPLE 17

2-Acetyl-2,3,3a,4,6,7-Hexahydro-3-[3-(trifluoromethyl)phenyl]-7-[[3-(trifluoromethyl)phenyl]methylene]thiopyrano[4,3-c]pyrazole-5,5-dioxide A suspension of 2,3,3a,4,6,7-hexahydro-3-[3-(trifluoromethyl)phenyl]-7-[[3-(trifluoromethyl)phenyl]methylene]thiopyrano[4,3-c]pyrazole-5,5-dioxide in 2ml of acetic anhydride and 25ml of acetic acid is heated on a steam bath for 15 minutes with occasional swirling. About 10ml of hot water is added and the solution is allowed to cool to room temperature. The solids are collected and washed with acetic acid/water (3/2) and water, and dried in vacuo over phosphorus pentoxide at 50°C to give 1.56g of the title compound, melting point 200°–202.5°C.

EXAMPLE 18

2,3,3a,4,6,7-Hexahydro-3-phenyl-7-(phenylmethylene)thiopyrano[4,3c]pyrazole

A mixture of 3.0g of tetrahydro-3,5-bis-(phenylmethylene)-4H-thiopyran-4-one and 385mg of anhydrous hydrazine in 150ml of ethanol is heated at reflux temperature for 30 minutes. Upon cooling to room temperature, the solids are collected and washed with ethanol to give 2.5g of the title compound, melting point 149°–155°C, dec.

EXAMPLES 19-25

Following the procedure of Example 1, but substituting the compound listed in column I for tetrahydro-3,5-bis-(phenylmethylene)-4H-thiopyran-4-one and the compound listed in column II for n-propyl hydrazine, yields the compound listed in column III.

| | Column I | Column II | Column III |
|---|---|---|---|
| 19 | tetrahydro-3,5-bis-[(4-acetylphenyl)methylene]-4H-thiopyran-4-one | benzyl hydrazine | 3-(4-acetylphenyl)-7-[(4-acetylphenyl)methylene]-2-benzyl-2,3,3a,4,6,7-hexahydrothiopyrano[4,3-c]pyrazole |
| 20 | tetrahydro-3,5-bis-[(4-cyanophenyl)methylene[-4H-thiopyran-4-one | ethyl hydrazine | 3-(4-cyanophenyl)-7-[(4-cyanophenyl)methylene]-2-ethyl-2,3,3a,4,6,7-hexahydrothiopyrano[4,3-c]pyrazole |
| 21 | tetrahydro-3,5-bis-[(4-nitrophenyl)methylene]-4H-thiopyran-4-one | n-octyl hydrazine | 2,3,3a,4,6,7-hexahydro-3-(4-nitrophenyl)-7-[(4-nitrophenyl)methylene]-2-octylthiopyrano[4,3-c]pyrazole |
| 22 | tetrahydro-3,5-bis-[[4-(dimethylamino)phenyl]methylene]-4H-thiopyran-4-one | phenyl hydrazine | 3-[4-(dimethylamino)phenyl]-7-[[4-(dimethylamino)phenyl]methylene]-2,3,3a,4,6,7-hexahydro-2-phenylthiopyrano[4,3-c]pyrazole |
| 23 | tetrahydro-3,5-bis-[(3-hydroxyphenyl)methylene]-4H-thiopyran-4-one | ethyl hydrazine | 2-ethyl-2,3,3a,4,6,7-hexahydro-3-(3-hydroxyphenyl)-7-[(3-hydroxyphenyl)methylene]thiopyrano[4,3-c]pyrazole |
| 24 | tetrahydro-3,5-bis-[(4-methylthiophenyl)methylene]-4H-thiopyran-4-one | benzyl hydrazine | 2-benzyl-2,3,3a,4,6,7-hexahydro-3-(4-methylthiophenyl)-7-[(4-methylthiophenyl)methylene]thiopyrano[4,3-c]pyrazole |
| 25 | tetrahydro-3,5-bis-[(4-ethylsulfinylphenyl)methylene]-4H-thiopyran-4-one | phenyl hydrazine | 3-(4-ethylsulfinylphenyl)-7-[(4-ethylsulfinylphenyl)methylene]-2,3,3a,4,6,7-hexahydro-2-phenylthiopyrano[4,3-c]pyrazole |

EXAMPLES 26–30

Following the procedure of Example 14, but substituting the compound listed in column I for acetic anhydride, yields the compound listed in column II.

|    | Column I | Column II |
|----|----------|-----------|
| 26 | benzoic anhydride | 2-benzoyl-2,3,3a,4,6,7-hexahydro-3-phenyl-7-(phenylmethylene)thiopyrano[4,3-c]pyrazole-5,5-dioxide |
| 27 | p-toluic anhydride | 2,3,3a,4,6,7-hexahydro-3-phenyl-7-(phenylmethylene)-2-(p-tolyl)thiopyrano[4,3-c]pyrazole-5,5-dioxide |
| 28 | 2-chlorobenzoic anhydride | 2-(2-chlorobenzoyl)-2,3,3a,4,6,7-hexahydro-3-phenyl-7-(phenylmethylene)-thiopyrano[4,3-c]pyrazole-5,5-dioxide |
| 29 | 4-methoxybenzoic anhydride | 2,3,3a,4,6,7-hexahydro-2-(4-methoxybenzoyl)-3-phenyl-7-(phenylmethylene)-thiopyrano[4,3-c]pyrazole-5,5-dioxide |
| 30 | 4-(trifluoromethyl)-benzoic anhydride | 2,3,3a,4,6,7-hexahydro-3-phenyl-7-(phenylmethylene)-2-[4-(trifluoromethyl)benzoyl]thiopyrano[4,3-c]-pyrazole-5,5-dioxide |

What is claimed is:

1. A compound having the formula

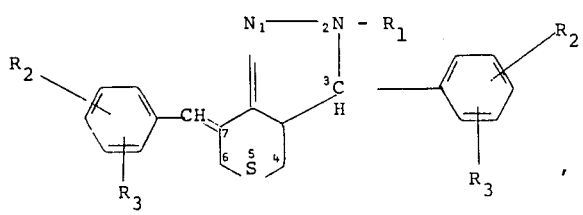

or a pharmaceutically acceptable acid addition salt thereof, or a 5-oxide or 5,5-dioxide thereof, wherein $R_1$ is hydrogen, alkyl, aryl, arylalkyl, or

wherein X is alkyl or aryl; and $R_2$ and $R_3$ are the same or different and are hydrogen, alkyl, hydroxy, alkoxy, alkylthio, alkylsulfinyl, trifluoromethyl, halogen,

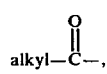

cyano, nitro or dialkylamino; wherein the terms alkyl and alkoxy refer to groups having 1 to 8 carbon atoms and the term aryl refers to phenyl or phenyl monosubstituted with an alkyl, alkoxy, halogen, or trifluoromethyl group.

2. A compound in accordance with claim 1 wherein $R_1$ is hydrogen.

3. A compound in accordance with claim 1 wherein $R_1$ is alkyl.

4. A compound in accordance with claim 1 wherein $R_1$ is aryl.

5. A compound in accordance with claim 1 wherein $R_1$ is arylalkyl.

6. A compound in accordance with claim 1 wherein $R_1$ is

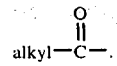

7. A compound in accordance with claim 1 wherein $R_1$ is

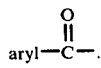

8. A compound in accordance with claim 1 wherein $R_2$ and $R_3$ are the same or different and are hydrogen, alkyl, alkoxy, trifluoromethyl, or halogen.

9. A compound in accordance with claim 1 wherein $R_2$ is hydrogen.

10. A compound in accordance with claim 8 wherein $R_2$ is hydrogen.

11. The compound in accordance with claim 1 having the name 2,3,3a,4,6,7-hexahydro-3-phenyl-7-(phenylmethylene)-2-propylthiopyrano[4,3-c]pyrazole.

12. The compound in accordance with claim 1 having the name 2,3,3a,4,6,7-hexahydro-3-(4-methoxyphenyl)-7-[(4-methoxyphenyl)methylene]-2-propyl-thiopyrano[4,3-c]pyrazole.

13. The compound in accordance with claim 1 having the name 3-(4-chlorophenyl)-7-[(4-chlorophenyl)methylene]-2,3,3a,4,6,7-hexahydro-2-propylthiopyrano[4,3-c]pyrazole.

14. The compound in accordance with claim 1 having the name 2,3,3a,4,6,7-hexahydro-3-phenyl-7-(phenylmethylene)-2-propylthiopyrano[4,3-c]pyrazole-5,5-dioxide.

15. The compound in accordance with claim 1 having the name 2,3,3a,4,6,7-hexahydro-3-phenyl-7-(phenylmethylene)-2-propylthiopyrano[4,3-c]pyrazole-5-oxide.

16. The compound in accordance with claim 1 having the name 2,3,3a,4,6,7-hexahydro-3-(4-methoxyphenyl)-7-[(4-methoxyphenyl)methylene]-2-propyl-thiopyran[4,3-c]pyrazole-5-oxide.

17. The compound in accordance with claim 1 having the name 3-(4-chlorophenyl)-7-[-(4-chlorophenyl)methylene]-2,3,3a,4,6,7-hexahydro-2-propyl-thiopyrano[4,3-c]pyrazole-5,5-dioxide.

18. The compound in accordance with claim 1 having the name 2,3,3a,4,6,7-hexahydro-3-(4-methoxyphenyl)-7-[(4-methoxyphenyl)methylene]-2-propyl-thiopyrano[4,3-c]pyrazole-5,5-dioxide.

19. The compound in accordance with claim 1 having the name 3-(3,4-dichlorophenyl)-7-[(3,4-dichlorophenyl)methylene]2,3,3a,4,6,7-hexahydro-2-propyl-thiopyrano[4,3-c]pyrazole.

20. The compound in accordance with claim 1 having the name 2,3,3a,4,6,7-hexahydro-2-propyl-3-[3-(trifluoromethyl)phenyl]-7-[[3-(trifluoromethyl)phenyl]methylene]thiopyrano[4,3-c]pyrazole-5,5-dioxide.

21. The compound in accordance with claim 1 having the name 2,3,3a,4,6,7-hexahydro-2-propyl-3-[3-(trifluoromethyl)phenyl]-7-[[3-(trifluoromethyl)phenyl]methylene]thiopyrano[4,3-c]pyrazole.

22. The compound in accordance with claim 1 having the name 2,3,3a,4,6,7-hexahydro-3-(2-methylphenyl)-7-[(2-methylphenyl)methylene]-2-propylthiopyrano[4,3-c]pyrazole.

23. The compound in accordance with claim 1 having the name 2,3,3a,4,6,7-hexahydro-3-phenyl-7-(phenylmethylene)thiopyrano[4,3-c]pyrazole-5,5-dioxide.

24. The compound in accordance with claim 1 having the name 2-acetyl-2,3,3a,4,6,7-hexahydro-3-phenyl-7-(phenylmethylene)thiopyrano[4,3-c]pyrazole-5,5-dioxide.

25. The compound in accordance with claim 1 having the name 3-(4-chlorophenyl)-7-[(4-chlorophenyl)methylene]-2,3,3a,4,6,7-hexahydro-2-phenylthiopyrano[4,3-c]pyrazole-5,5-dioxide.

26. The compound in accordance with claim 1 having the name 2,3,3a,4,6,7-hexahydro-3-[3-(trifluoromethyl)phenyl]-7- [[3-(trifluoromethyl)phenyl]methylene]thiopyrano[4,3-c]pyrazole-5,5-dioxide.

27. The compound in accordance with claim 1 having the name 2-acetyl-2,3,3a,4,6,7-hexahydro-3-[3-(trifluoromethyl)phenyl]-7-[[3-(trifluoromethyl)phenyl]methylene]thiopyrano[4,3-c]pyrazole-5,5-dioxide.

28. The compound in accordance with claim 1 having the name 2,3,3a,4,6,7-hexahydro-3-phenyl-7-(phenylmethylene)thiopyrano[4,3-c]pyrazole.

* * * * *